(12) United States Patent
Butler et al.

(10) Patent No.: US 7,959,132 B2
(45) Date of Patent: Jun. 14, 2011

(54) APPARATUS FOR EMITTING A CHEMICAL AGENT

(75) Inventors: Martin Butler, Hull (GB); Richard Read, Slough (GB); Christopher Smith, Macclesfield (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 1147 days.

(21) Appl. No.: 10/558,665

(22) PCT Filed: Jun. 2, 2004
(Under 37 CFR 1.47)

(86) PCT No.: PCT/GB2004/002359
§ 371 (c)(1),
(2), (4) Date: Dec. 7, 2006

(87) PCT Pub. No.: WO2004/105819
PCT Pub. Date: Dec. 9, 2004

(65) Prior Publication Data
US 2007/0257130 A1    Nov. 8, 2007

(30) Foreign Application Priority Data

Jun. 2, 2003 (GB) .................................. 0312561.4
Oct. 10, 2003 (GB) .................................. 0323788.0

(51) Int. Cl.
*B01F 3/04* (2006.01)

(52) U.S. Cl. .............................. 261/30; 261/99; 261/104
(58) Field of Classification Search .................... 261/30, 261/99, 104, 107, DIG. 88
See application file for complete search history.

(56) References Cited

U.S. PATENT DOCUMENTS

| | | | | |
|---|---|---|---|---|
| 1,323,462 A | * | 12/1919 | Flanders | 422/124 |
| 1,879,358 A | * | 9/1932 | Lilly | 261/104 |
| 1,911,871 A | * | 5/1933 | Andersen | 422/124 |
| 2,164,763 A | * | 7/1939 | Buck | 261/30 |
| 4,370,300 A | | 1/1983 | Mori et al. | |
| 5,000,383 A | | 3/1991 | van der Heijden | |
| 5,662,835 A | | 9/1997 | Collingwood | |
| 6,371,450 B1 | | 4/2002 | Davis et al. | |
| 6,631,888 B1 | * | 10/2003 | Prueter | 261/30 |
| 6,766,817 B2 | | 7/2004 | Dias da Silva | |
| 6,918,404 B2 | | 7/2005 | Dias da Silva | |
| 6,938,883 B2 | * | 9/2005 | Adams et al. | 261/30 |
| 7,032,831 B2 | * | 4/2006 | Duston et al. | 239/44 |
| 7,036,800 B2 | * | 5/2006 | Ellis | 261/26 |
| 7,066,586 B2 | | 6/2006 | Dias da Silva | |
| 7,244,398 B2 | * | 7/2007 | Kotary et al. | 422/124 |
| 7,341,698 B2 | * | 3/2008 | Pedrotti et al. | 422/123 |

FOREIGN PATENT DOCUMENTS

| | | |
|---|---|---|
| EP | 813360 A | 9/1996 |
| GB | 2 181 649 A | 4/1987 |
| WO | WO 01/21226 | 3/2001 |

OTHER PUBLICATIONS

International Search Report dated Sep. 21, 2004 for application PCT/GB2004/002359.
Written Opinion for application PCT/GB2004/002359.

* cited by examiner

*Primary Examiner* — Scott Bushey
(74) *Attorney, Agent, or Firm* — Andrew N. Parfomak; Norris McLaughlin & Marcus, PA

(57) ABSTRACT

Apparatus for emitting a chemical agent as a vapour which apparatus includes operative parts and a decorative cover. The decorative cover has curved air inlet channels. The operative parts include a reservoir containing the chemical agent in liquid form; a wick in communication with the chemical agent; an emanator carried by the wick and located outside the reservoir and a fan, preferably battery-powered, to impel air over the emanator.

22 Claims, 15 Drawing Sheets

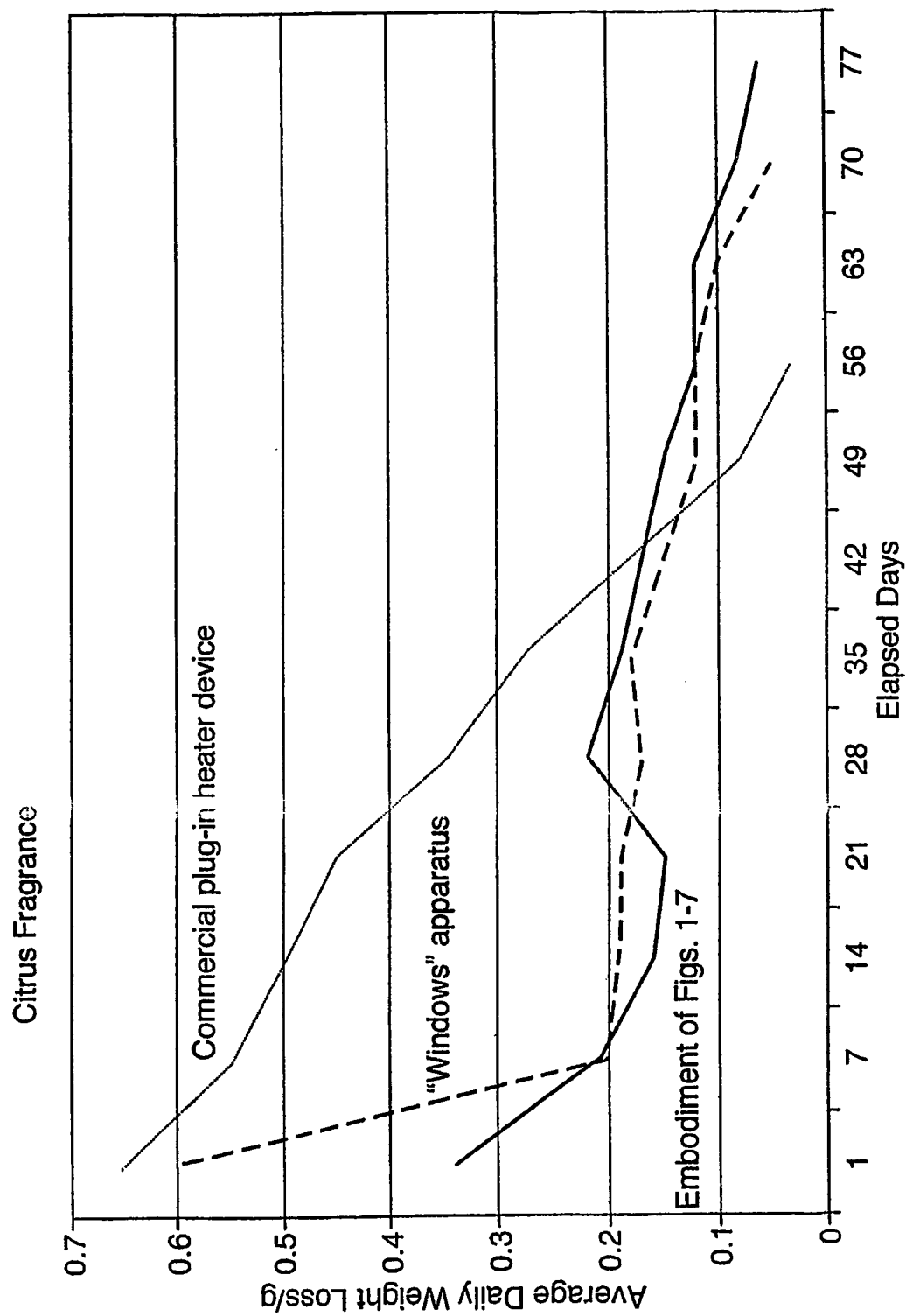

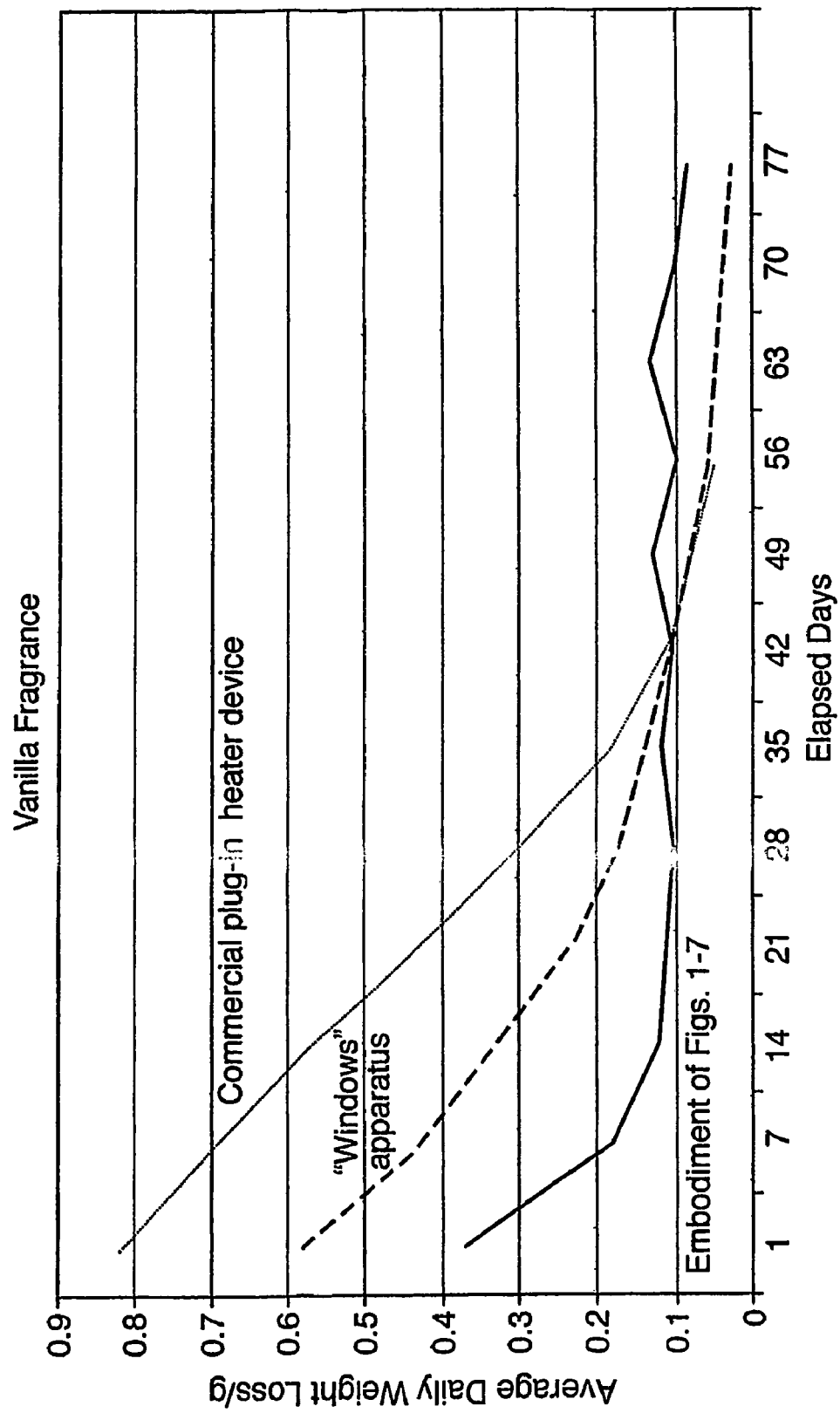

Project Belt
Spring-loaded emanators
Sweet Spring B

APPARATUS FOR EMITTING A CHEMICAL AGENT

This invention relates to an apparatus for emitting a vapour, and to a method of delivering a vapour to an air space.

Many different types of apparatus for emitting a vapour are available.

Some traditional devices employ naked flames, for example fragranced candles or devices heating an oil/water bath.

One very common type of device is a simple passive evaporation device. At the commencement of use a supply of the required chemical agent is exposed to the atmosphere, and starts to evaporate. Generally once operation has commenced the consumer has no means for controlling the rate of release of the vapour.

A further type of apparatus employs an electrical heater and is plugged in to a mains electrical supply socket. A heat emitter is provided, to assist the evaporation. It has been proposed to control the level of evaporation by controlling the delivery of heat to the emanator from which evaporation takes place. For example in WO 01/21226 the user may operate a slider which controls the position of a cylindrical barrier part which may be interposed between the emanator and the source of heat.

The electrical devices are quite effective, and popular, but the control over their operation is not always very accurate.

EP-A-813360 describes a further type of vaporising apparatus, this time employing batteries which operate a fan. The apparatus has a plug-in cartridge which comprises a reservoir of the chemical agent to be evaporated, batteries, a cylindrical wick extending from the reservoir and separate emanator hinged to the cartridge, between a stowed position in which the cartridge occupies a minimum of space and an operative position in which it projects outwardly from the top of the cartridge, and has been brought into contact with the upper end of the wick. When in this outward position it is over the fan. Moreover it has through-bores, so that when the fan is operated air is blown through the emanator, carrying away molecules of the chemical agent which have been drawn into it by capillary action.

However there is no provision in EP-A-813360 to alter the output, other than by pivoting the emanator so that the connection between the wick and the emanator is broken altogether. In other words the apparatus is essentially either on or off. Furthermore the provision of a pivoting emanator is somewhat complicated and expensive and the correct operation of the apparatus depends upon the formation of a good contact between the exposed end of the wick, and the emanator. It is not easy to design an apparatus in which this good contact, to be brought about by the operation of the consumer, is assured.

In accordance with a first aspect of the present invention there is provided apparatus for emitting a chemical agent as a vapour, the apparatus comprising:
  a reservoir containing the chemical agent in liquid form;
  a wick in communication with the chemical agent;
  an emanator carried by the wick and located outside the reservoir; and
  an electrically operable fan to impel air over the emanator.

Preferably the apparatus includes battery means to operate the fan. However mains operated apparatus in accordance with the present invention is not excluded.

Preferably the chemical agent is selected from a fragrance, non-fragrancing deodoriser, decongestant, insecticide, insect repellent, anti-allergenic agent and sanitiser.

Preferably the emanator is carried at the top of the wick, that is, at the distal end of the wick. Preferably the proximal end of the wick is immersed in the chemical agent until the chemical agent is exhausted.

Preferably the emanator is a body which has one, or preferably more, surfaces over which air flows. For example it may have one or, preferably, two generally planar surfaces, transverse to the wick. Preferably the or each such surface is substantially perpendicular to the wick. Preferably the or each such surface is of area in the range 400-1600 $mm^2$, more preferably 600-1200 $mm^2$.

Preferably the emanator and the wick are generally T-shaped in cross-section taken along the axis of the wick.

Preferably the emanator is circular in plan view.

Preferably the emanator is larger in cross section than the wick. Preferably the area of the emanator, in plan view, is at least two times the cross-sectional area of the wick, more preferably at least four times, and most preferably at least six times.

Preferably the emanator is so located that, in use, air is able to flow over the top of it, preferably transversely. More preferably, air is able to flow underneath it as well as over the top of it. Air is preferably able to flow across the emanator, preferably from side to side. For example the reservoir preferably has an upper wall through an aperture in which the wick extends; and the emanator is held in spaced relation from that upper wall. Air may flow over the top of the emanator but also through the space between the upper wall of the reservoir and the underside of the emanator. In embodiments in which air is able to flow only over the top of the emanator, the emanator may suitably be located against said upper wall, preferably in a seating provided therefor. As indicated above other arrangements may be envisaged, permitting flow over a plurality of surfaces (we include within this definition respective parts of a spherical or ovoid surface).

The emanator may be operable to move between a first, inoperative, configuration and a second, operative, configuration.

The operative configuration preferably allows air flow around and/or across the emanator.

The emanator may be adapted to be moved between the first and second configurations by a resilient bias, which may be a spring, preferably a conical spring.

The emanator may be biased towards the second configuration.

The first configuration may be a lowered configuration. The second configuration may be a raised configuration.

The emanator may be operable to move relative to the wick, preferably by action of the resilient bias. The emanator may incorporate a collar adapted to allow movement relative to the wick.

The emanator may be held in the first configuration by a cover, which may be securable to the reservoir. The emanator is preferably arranged to move to the second configuration on removal of the cover.

The wick, when in the second configuration, has advantageously good emanation characteristics due to enhanced air flow characteristics compared to fixed position emanators. Air can advantageously flow transversely across one or both major faces of the emanator, which may be upper and lower faces, from one side to another.

The emanator may comprise a series of projections, preferably formed by cut outs. The projections may be radial spokes. The emanator may be made of a deformable material, which may adopt the second configuration by movement to a preferred orientation.

Preferably the emanator, as well as the wick may be an ordinary capillary body, for example formed by hot pressing, extrusion or sintering of a fibrous material, for example polyolefin fibres.

Preferably the emanator does not have any non-capillary through-bores.

Preferably the opening is formed by a number of lobed walls. For example when there are four lobed walls the opening would then be of quadrifoliate form, with portions which engage the wick, to hold it in place, and four small openings, at 90° intervals.

Preferably the amount of the chemical agent present at the start of operation is in the range 10-40 ml, more preferably 12-25 ml.

Preferably the apparatus of the invention is designed for good operation over a period of at least 30 days.

Preferably the amount of chemical agent which is evaporated per day by the apparatus of the invention does not vary by more than four-fold, between the first day of operation and (as a reference) the twentieth day.

Preferably the amount of chemical agent which is evaporated per day by the apparatus of the invention does not vary by more than two-fold, between the seventh day of operation and (as a reference) the twentieth day.

Preferably the amount of chemical agent which is in total evaporated during the first week of operation, is not more than three times the amount which is evaporated during the fourth week of operation, under identical operative conditions of the apparatus and under identical ambient conditions.

When the emanator has more than one operative condition (for example "high" and "low") the definitions herein as to output are met by at least one such condition. Preferably they are met by all such conditions.

Preferably the apparatus can be set such that the amount of chemical agent evaporated does not exceed 0.6 g/day for any day of its operation, and preferably does not exceed 0.4 g/day.

Preferably the apparatus includes a base on which are mounted the fan, and a motor therefor. Preferably the base is formed with a socket to receive the bottom region of a cartridge, comprising the reservoir and a battery compartment. Such a cartridge may be supplied as a refill.

Preferably the upper wall of the reservoir has an aperture which is slightly oversized, for the wick. This is to permit venting and also to allow any chemical agent on top of the reservoir to drain back into it, for example when a refill cartridge comprising the reservoir, capped, has been inverted, during transportation or storage.

Preferably the reservoir, or the cartridge comprising the reservoir and the battery compartment, fits into the base in a snap-fit manner. This may be achieved by means of elastically deformable tabs, lips, ridges or the like which can slide past each other. Preferably a firm fit is thereby achieved, to provide a high level of security against unintended separation, and against spillage.

Preferably the reservoir, preferably within a cartridge when provided, is formed with a deflection surface generally facing the fan. The deflection surface may be aligned wholly with the fan but is preferably aligned only partially with the fan. The deflection surface is present to deflect impelled air out of a smooth upwards pathway towards the outlet of the apparatus, and/or to introduce or increase turbulence. Preferably the deflection surface is an undercut or overhanging wall portion formed in a side wall of the reservoir. In one effective embodiment it may be transverse, preferably substantially perpendicular, to the upward air pathway from the fan. In another embodiment it is oblique or slanted to the upward air pathway from the fan. In each case it is provided to ensure that air flows a tortuous pathway between the fan and the outlet and/or that the airflow has a high degree of turbulence.

Preferably the fan is located generally on one side of the device and the outlet is located generally on the other side of the device, the former preferably being at a low position and the latter preferably being at a high position; and with the emanator being located between them, such that the impelled air must pass the emanator to reach the outlet.

The deflection surface, when provided, is preferably so located as to urge impelled air away from the emanator.

The apparatus includes a cover, and the cover contains the outlet mentioned above, together with air inlets. The cover is a decorative part and screens the operative parts from view. A user may select a different design or colour of cover, without changing the operative parts.

A cover suitably fits over the operative parts, being open at its base to allow the operative parts to pass, preferably until the cover and operative parts engage positively together.

Preferably the reservoir and emanator are provided with a removable cap, which prevents evaporation of the chemical agent during transport and storage. The removable cap may conveniently be a screw cap. Preferably the removable cap is too large to permit the cover to receive the operative parts with the cap on. Thus, the user is compelled to remove it before the assembling the apparatus for operation.

We have found, to our surprise, that the cover, though designed as a decorative part, is of importance in obtaining good performance. We have obtained an excellent profile of steady evaporation rate as a function of time when the cover has a plurality of inlet air channels, which may alternatively be called air guides, or injectors, or louvres, or chutes, or restrictors (as opposed to window-like openings); and/or in which the cover has openings which introduce air into the interior space inside the cover in one or more directions generally transverse to the direction(s) in which air leaves the cover, through the outlet.

Preferably the cover has two identifiable main sides, each containing at least one inlet air channel, and preferably a plurality of inlet air channels; and a front wall containing the outlet, preferably at an upper position thereof.

Preferably each inlet air channel is of slit form and comprises opposed, overlapping surfaces.

Preferably each inlet air channel is curved, with each main side of the cover having first and second inlet air channels which are curved such that their convexity faces each other.

Preferably the inlet air channels are such that air drawn through them must follow a non-straight, preferably sinuous pathway.

Preferably the cover is such that when it is viewed from the front the interior of the cover is occluded from view.

Preferably the inlet air channels are substantially the only route for air to enter the apparatus.

In addition, as mentioned above, the user may purchase refill packs of the chemical agent, preferably supplied with new batteries in a one-part pack. Preferably the operation is such that exhaustion of chemical agent coincides with exhaustion of the batteries.

Preferably the battery compartment is factory-sealed. Preferably it has a frangible closure, apertured to enable the required electrical contacts to be made. By frangible closure we mean that it must be broken in order to remove the batteries. Preferably it cannot thereafter be restored. The provision of a frangible closure encourages the consumer to use the batteries provided, these being selected to become exhausted on or shortly after exhaustion of the chemical agent. It also facilitates recycling of the batteries, once exhausted.

In an alternative embodiment the battery compartment could be accessed by the consumer, and batteries removed. In such an embodiment at least one end of the battery compartment, preferably the lower end, is formed in such a way that only the correct battery terminal may be received; for example a positive terminal on one side and a negative terminal on the other side. The sides may be positively separated, for example by a divider wall.

Preferably the operation of the apparatus is controllable. In one embodiment it could be controlled by fan speed. Preferably, however, it is controlled by controlling the periods for which the fan operates. Thus, the apparatus may include an electronic timing circuit. In one embodiment its mode of operation may be as follows:

- passive operation—fan off. Some natural evaporation is likely to take place from the emanator.
- medium-level operation—short bursts of fan operation, separated by non-operation, and controlled by the timing circuit.
- boost operation—longer periods of fan operation and/or shorter periods in between than in regular operation, and controlled by the timing circuit.

Many operational regimes could be defined by the timing circuit.

The device is designed such that when operated throughout its life at regular operation the evaporation of the chemical agent is complete within 25-80 days, preferably 40-60 days.

An operational regime in which the fan operates continuously is not excluded but is not likely to be desirable, except perhaps in constantly odoriferous environments. Aside from the shorter lifetime of the reservoir and batteries the benefit of such operation may be reduced, in fragrancing embodiments, by the phenomenon known as anosmia or nasal attenuation. This does not matter in the case of an insecticide, for example, but when the chemical agent is a fragrance, the perception of that fragrance by the user is more pronounced when it is delivered in bursts.

We have found that the delivery of chemical agents in bursts, in a preferred apparatus of the present invention, including a timing circuit, is in all cases advantageous in terms of achievement of good output control, but in the case of a fragrance this is particularly beneficial in avoiding nasal attenuation.

Preferably the fan stands proud of the motor, to aid free running of the fan.

In accordance with a second aspect of the present invention there is provided a method of delivering a vapour into an air space, by use of an apparatus of the first aspect of the invention.

According to a further aspect of the invention there is provided apparatus for emitting a chemical agent as a vapour, the apparatus comprising:

- a reservoir containing the chemical agent in liquid form;
- a wick in communication with the chemical agent;
- an emanator in fluid communication with the wick and located outside the reservoir;
- wherein the emanator is operable to move between a first, inoperative, configuration and a second, operative, configuration.

The second configuration preferably allows air flow around the emanator, whereas the first configuration preferably has substantially restricted air flow around the emanator.

All of the features described herein may be combined with any of the above aspects, in any combination.

The invention will now be further described, by way of example, with reference to the accompanying drawings, in which FIG. 1 shows an emanator in accordance with the present invention in side elevation, predominantly showing the cover thereof;

FIGS. 8 and 9 are graphs showing the output of the apparatus of the present invention in comparison with other apparatus, for two different fragrances;

Figure 1:
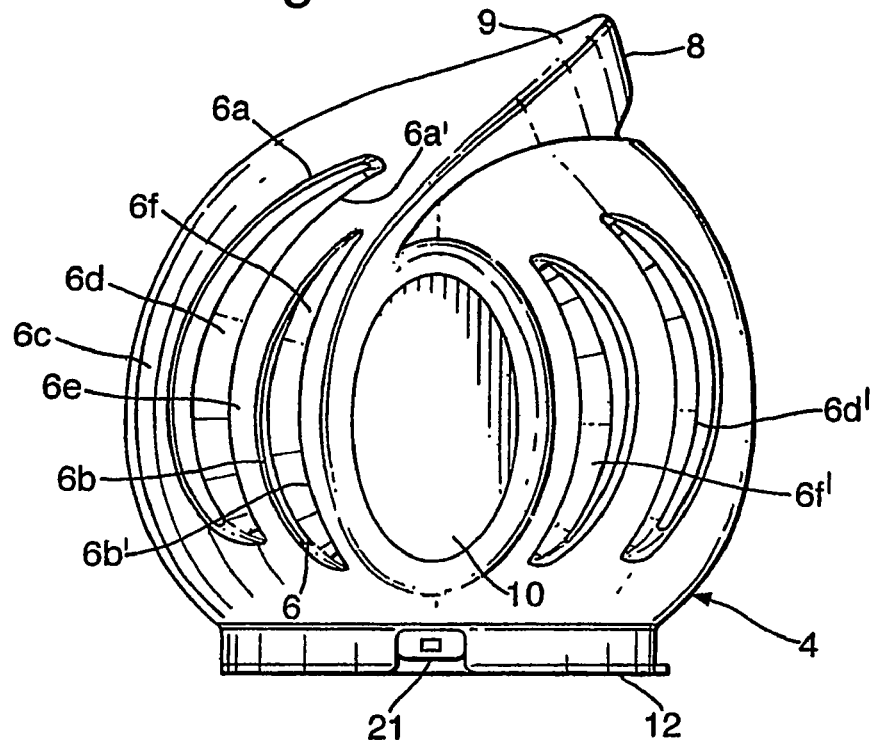
Figure 2:
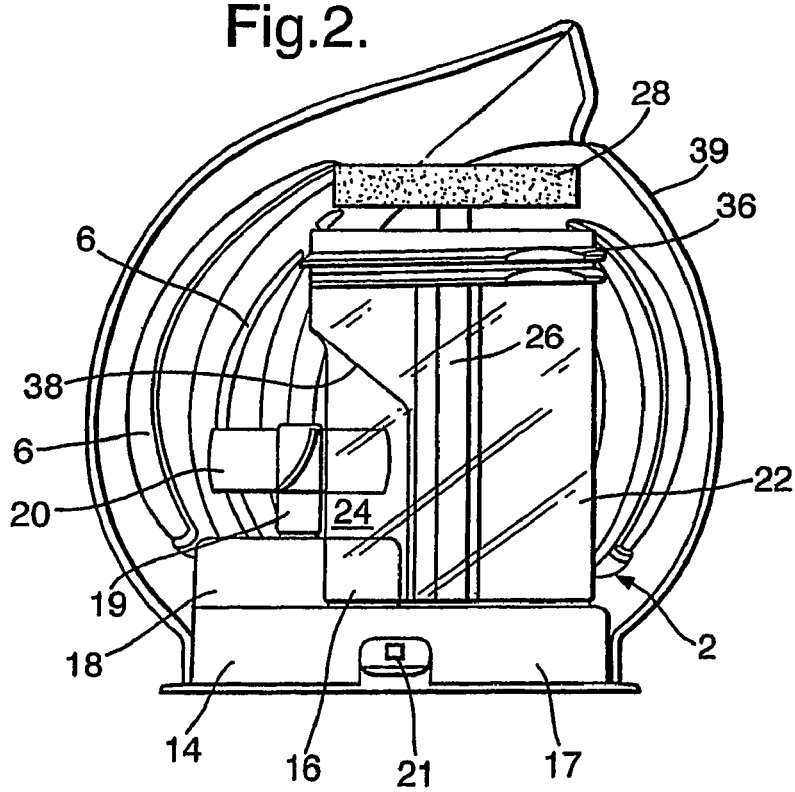
FIG. 2 is a corresponding view with a cover removed (and placed behind the operative parts of the apparatus, to show the scale and arrangement of the operative parts)

The apparatus comprises operative parts 2 shown in FIG. 2, covered by a cover 4, shown in FIG. 1. The cover has outwardly curved front and rear walls each of which has a series of curved slots 6 which are of attractive appearance, but which also function as inlet air channels. It also has a smaller vent 8 at its uppermost front-facing region. It can be seen that the cover tapers towards the vent 8, so that it has the form of a funnel 9, leading to the vent 8. The cover has on each curved wall a central oval region 10. On the side shown in FIG. 1 this is open so that the consumer can see the operative parts inside, and determine the status of the apparatus by eye. However although open it does not function as an inlet vent, being largely occluded by the operative parts. On the other side the corresponding central oval region is in the form of a panel.

In FIG. 1 the elevations of the openings of the air channels are shown shaded, with the surrounding structure of the cover shown in white. It can be seen that there are four inlet air channels on the side of the cover shown. They are arranged in pairs, curved generally around the central oval region 10, with smaller inlet air channels nearer to the oval region, and larger ones further from it. Each inlet air channel could be described as crescent-shaped, or banana-shaped. There are four corresponding inlet air channels in the side not shown.

Figure 6:
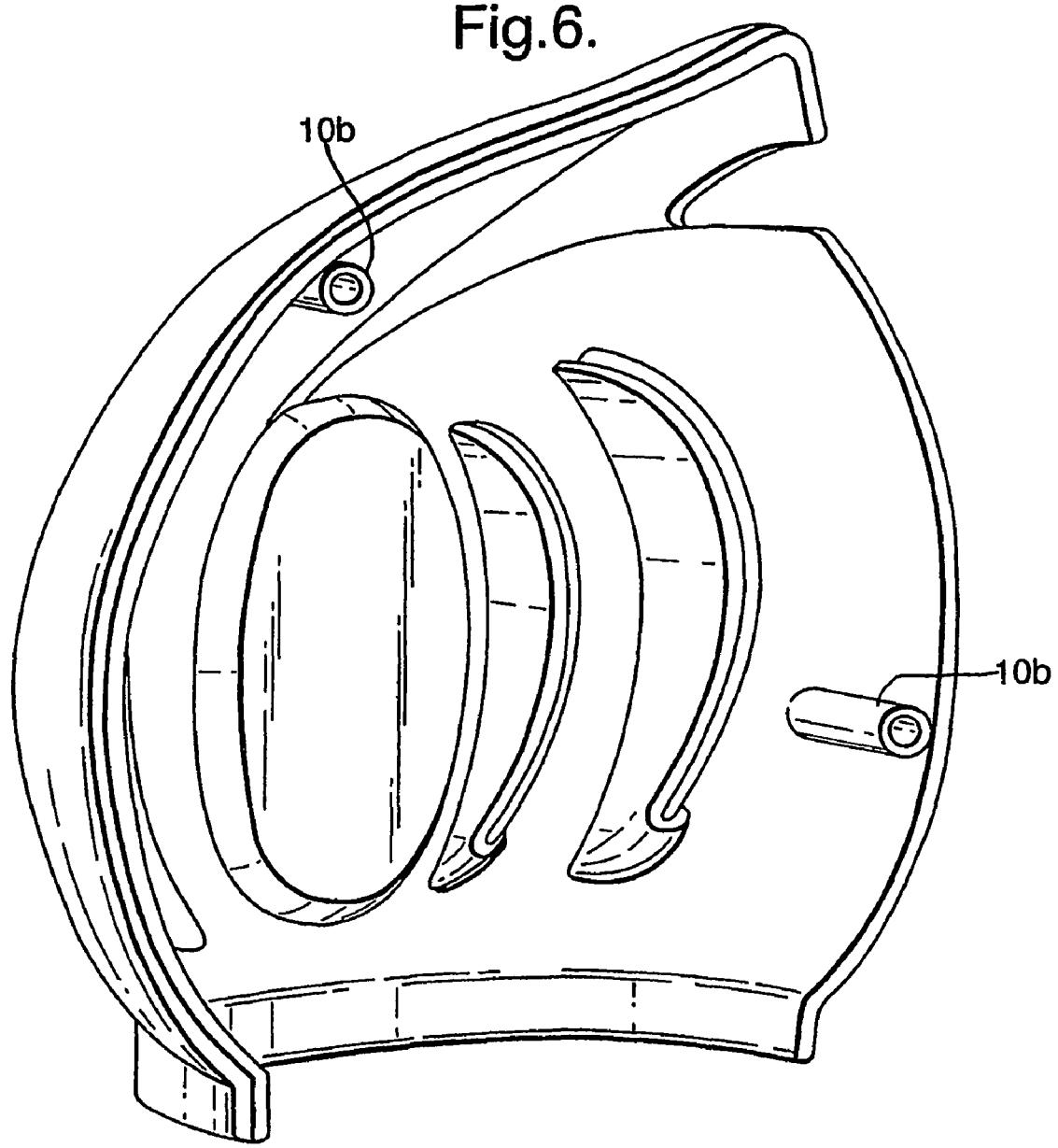
FIG. 6 shows the inside of one half of the cover.
Figure 7:
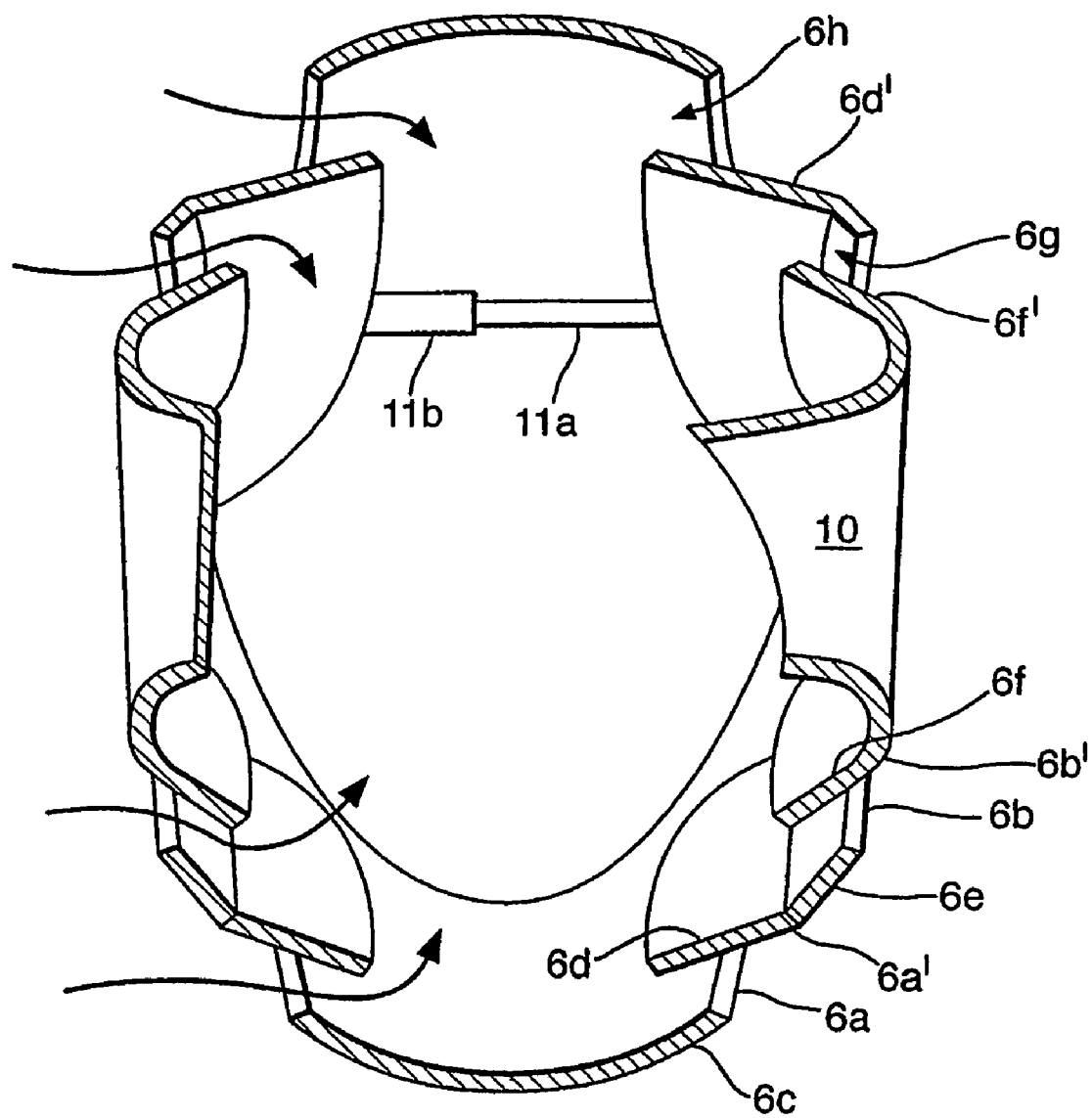
FIG. 7 is a cross-section of the cover along line X-X shown in FIG. 4.

Each inlet air channel has frontal curved edges 6a, 6a', 6b, 6b' and so on—see FIG. 6; also FIGS. 1, 7. By frontal we mean at the inlet side of the respective inlet air channel, that is, on the exterior side of the cover. Depending from each frontal curved edge is a solid wall portion of the cover. This may be a part of the cover wall proper—for example part 6c in the case of edge 6a—or a flared part depending from the edge—for example parts 6d in the case of edge 6a'; 6e in the case of edge 6b; 6f in the case of edge 6b'.

Each inlet air channel is designed such that one edge overlaps said solid wall portion. In other words air passing through the inlet air channel must flow between the edge (and the solid wall portion depending from the edge), and the aforementioned solid wall portion; which thereby form a pair of louvres, defining between them what may be called a channel.

This "overlap" feature is best illustrated by the inlet air channels indicated as 6g and 6h in FIG. 7.

The cross-sectional area of the eight air inlet channels is approximately 24 cm² in total.

As a result of the constructional features described above air follows a sinuous pathway in entering the apparatus, as schematically indicated by the arrows through the left-hand channels shown in FIG. 7. Although the inside of the cover can be seen through the channels in the side view of FIG. 1, (the shaded regions) it is not believed to be the case that air will flow straight into the apparatus without being deflected in the manner described above.

Figure 5:
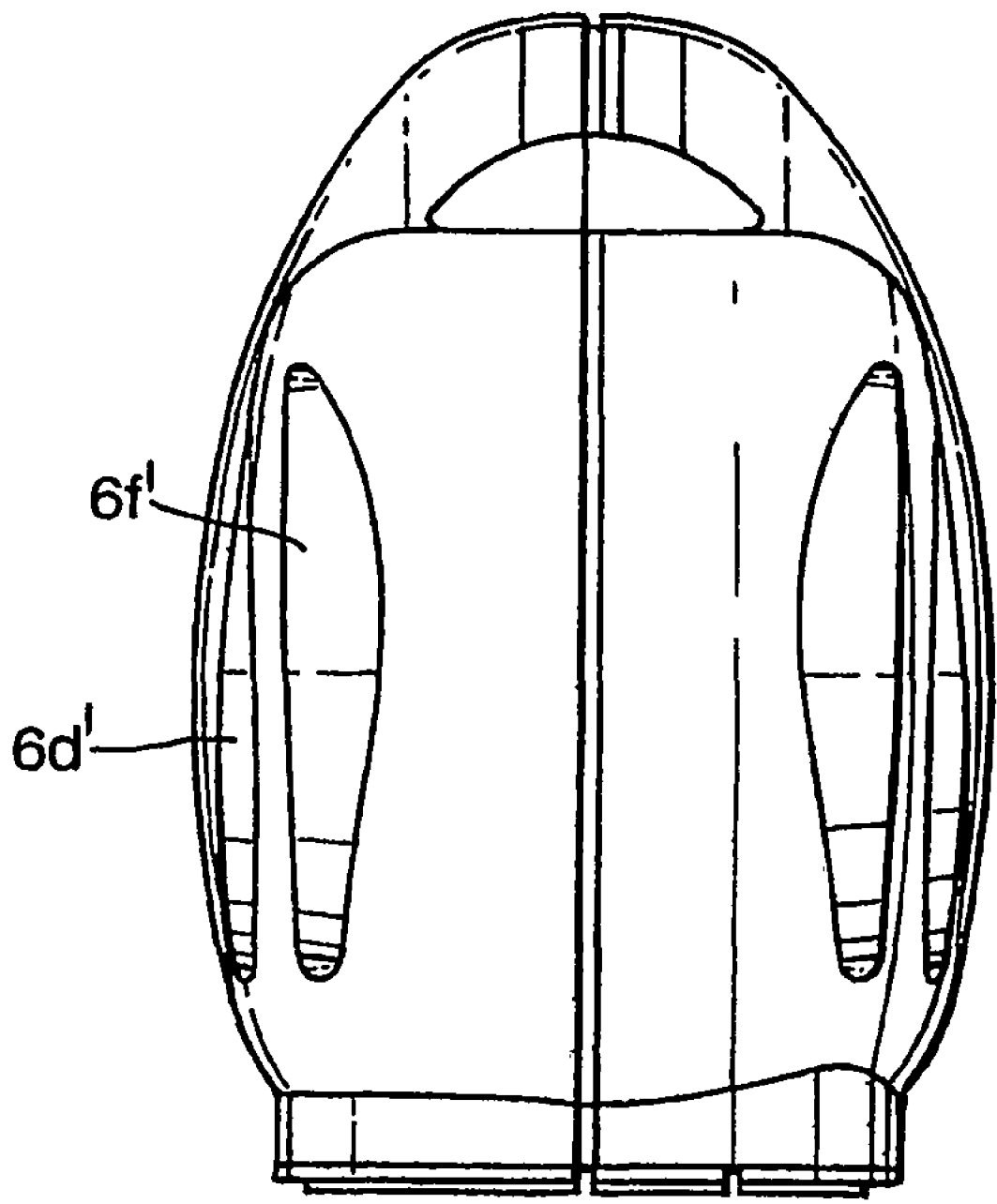
FIG. 5 shows the cover in front elevation.

When viewed from the front (see FIG. 5) the interior of the cover cannot be seen due to the overlaps described above. What can be seen in this view is not the inlet air channels, but the flared depending parts 6d', 6f'—see also FIG. 1.

Figure 4:
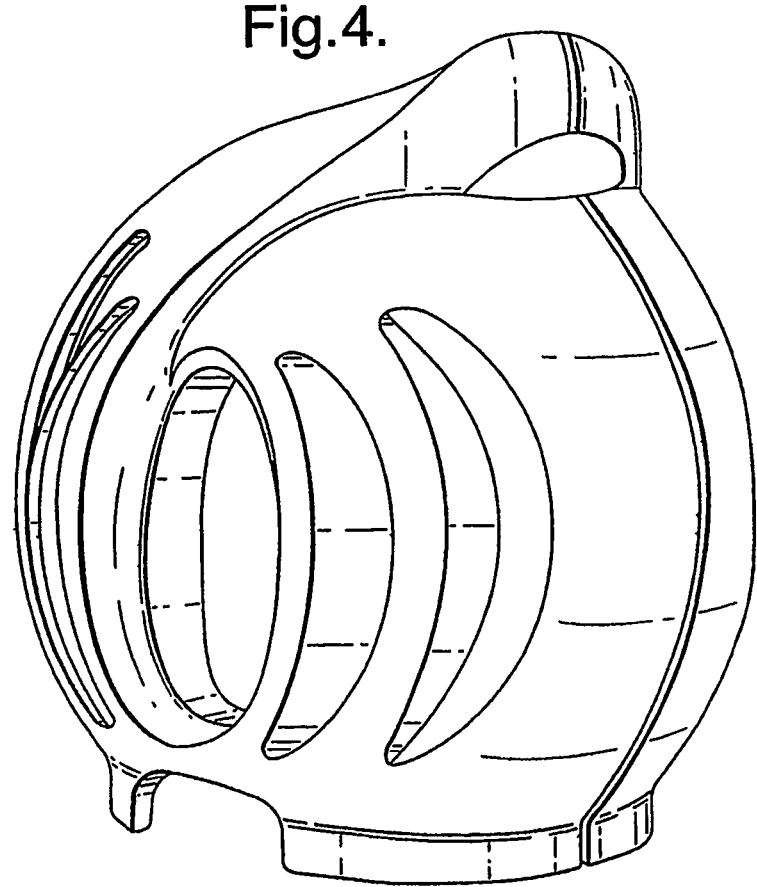
FIG. 4 shows the cover in perspective view.

The cover is moulded as two shells, with male-female formations (11a, 11b—FIGS. 6, 7) which enable them to be press-fitted together. The join line can clearly be seen in FIGS. 4 and 5.

At its base the cover terminates in a socket formation 12, by means of which it may be fitted over the operative parts.

The operative parts shown in FIG. 2 comprise a base unit 14 and a cartridge 16, which fits into the base unit.

The base unit comprises a lowermost plinth 17, which has an upstanding side wall onto which the socket formation 12 of the decorative cover 4 fits, in a mild interface fit.

A motor 18 is mounted on the base unit. The motor 18 in turn has mounted on it a fan 20. It will be observed that the fan 20 is carried proud of the motor 18 by an axle 19.

Within the base unit 17 is contained a simple electronic (PCB) timing circuit (not shown), to control the motor. The user controls the motor, via the circuit, using a switch 21 but on the front of the base unit, and accessible through the cover. This has off, regular and boost positions, which give vapour outputs that may be described as low (or passive), medium and high.

The base unit 17 is formed with a socket into which the cartridge 16 fits, in a snap-fitting manner.

Figure 3:
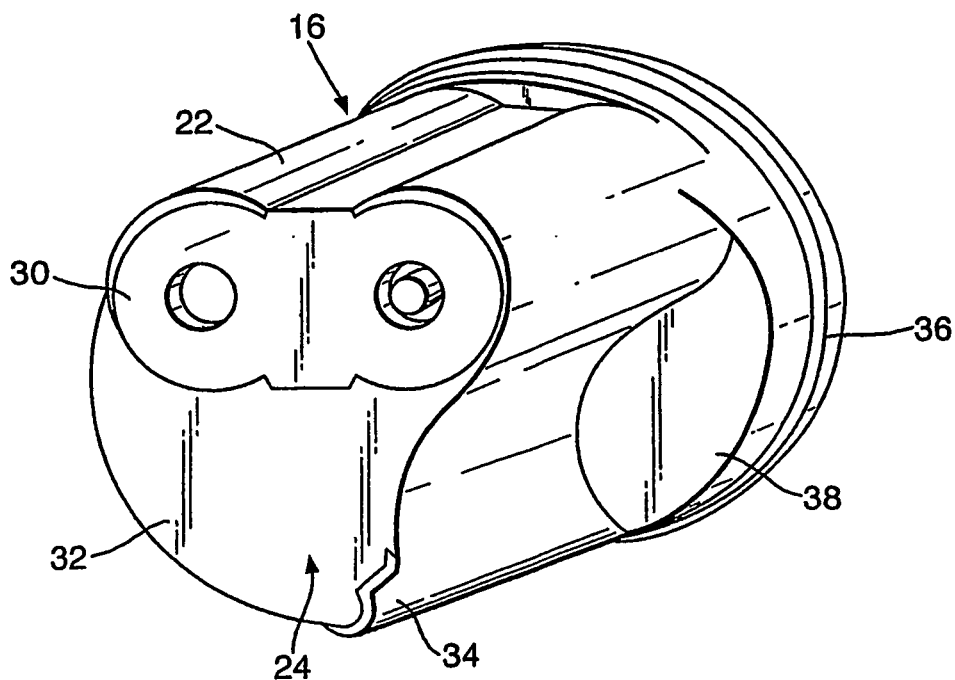
FIG. 3 shows a perspective view of a replacement cartridge for use in the apparatus.

The cartridge 16 is shown in FIG. 2 but also, detached from the rest of the apparatus, in FIG. 3.

The cartridge has a battery compartment 22 (indicated by dotted lines in FIG. 3); a reservoir 24 for evaporable chemical agent; a relatively thin cylindrical wick 26 (shown in close hatching in FIG. 2) which extends from the bottom of the reservoir, and through an aperture in its upper wall; and a disc-shaped emanator 28 carried at the distal end of the wick 26. The wick and emanator are of a capillary material, without any non-capillary through-bores.

The battery compartment is designed to take two AA batteries. It is closed by a separately formed bottom wall 30. It is a factory sealed unit. The bottom wall 30 has openings to allow the required electrical contacts to be made. Removing the bottom wall breaks it in such a manner that it cannot be replaced.

The reservoir has a bottom wall 32 which is co-moulded in the one operation with the side walls of the cartridge. It can be seen in FIG. 3 that one of its side walls 34 is sigmoidal in cross-section, but that the upper end of the cartridge, at rim 36, is circular. Between the sigmoidal wall 34 and the upper rim 36 the reservoir has an undercut inclined wall 38. This can also be seen in FIG. 2. Thus the reservoir has an overhanging wall portion projecting towards the flow pathway, above the fan, and overhanging about one half of it.

The top wall of the reservoir is not shown but it essentially has a quadrifoliate opening through which the wick passes. The four curved edges of the opening grip the wick and four spaces are left, for venting or draining purposes. The opening thus helps to keep the wick in place and in addition the wick rests against the inside wall of the battery compartment (as can just be seen in FIG. 2). In addition there is a small cup formation (not shown) in the bottom wall of the reservoir, for the wick end to stand in.

In this embodiment the emanator 28 is a circular disc of diameter 33 cm, and thickness 5 mm. In contrast the diameter of the wick is 5.2 mm. There is a gap 39 of 5 mm between the emanator 28 and the upper wall of the reservoir. The diameter of the emanator is substantially the same as the internal diameter of the rim 36 of the cartridge.

To use the device, the cover is located in place, with the socket 12 over the plinth 17. If the user selects the regular or boost positions, the timer circuit controls the on/off regime of the motor. For example for regular operation the motor might have a repeating regime of "1 minute on, 5 minutes off" whilst in the boost position it may have a repeating regime of "1 minute on, 2 minutes off". When the motor is operating the fan impels air upwards. The overhanging wall portion 38 is close by the fan and will serve to deflect air and/or to increase the turbulence of the air flow, within the apparatus. For reasons which are not understood it improves the operation of the device, even though it may be expected to hinder the flow of air to the emanator. By a tortuous route from the fan 20 to the vent 8 air flows past the emanator, presumably in a highly turbulent manner. It will be seen that there is provision for air flow above and below the emanator surface. Permitting air to flow beneath the emanator has also been found to provide benefit in achieving a controllable device, again, without the reason being clear. Air, charged with evaporated chemical agent, reaches the vent 8, via the funnel 9, and passes through the vent 8, into the external air space.

The apparatus is designed such that when the chemical agent is exhausted this should coincide with exhaustion of the batteries. If this does not happen precisely the chemical agent will be exhausted first, with the batteries having very little further viability. The user may purchase a replacement cartridge, with the same or difference volatile chemical agent, and already containing fresh batteries. This replacement cartridge contains a new wick and emanator. To prevent loss during transportation and shop display the replacement cartridge is closed by a screw-threaded cap (not shown). The screw threads on the cartridge can be seen as 40 in FIGS. 2 and 3. The user simply removes and discards this cap, holding the cartridge upright, and then introduces the cartridge into the socket in the plinth, replaces the cover, and the recharged device is ready for use. The cap is of a size that when it is in place the cover cannot be located over the operative parts.

FIGS. 8 and 9 give an indication of the performance of the embodiment described above, using two different fragrances, a citrus fragrance and a vanilla fragrance. This embodiment was used in its passive emanation mode, in comparison with a corresponding device as described above, also of the invention, but having open "windows" in the cover, not air inlet channels. The "windows" were located similarly to the air inlet channels of the first embodiment. Both covers had an open air area of 24 cm², in total. Both had 15 cm³ of the specified fragrance. Also tested was a commercial plug-in device having a heater to promote evaporation used to its minimum heat setting, and having 21 cm² of the fragrance, not having a fan or a cover, and not of the invention.

The results achieved by the apparatus of FIGS. 1-7 are remarkably level. It can be seen that even in the early phase, the emanation rate was much less than for the other devices. The results for the device with the open "windows" cover are better than the commercial plug-in product, but not as good as those achieved by the apparatus of FIGS. 1-7.

In another embodiment there is no gap between the emanator and the upper wall of the reservoir. The emanator may rest on the upper wall or ledge, which forms a seating for the emanator. This arrangement leads to slower emanation and may be more secure against spillage, than the one shown in FIGS. 1-7.

In another embodiment there is an undercut wall which is transverse to the fan axis, preferably perpendicular, rather than inclined, as in the case of the wall 38 shown in FIG. 2. A transverse undercut wall may be expected to produce greater turbulence, which may lead to operational benefits.

In another embodiment the battery housing is not shown in FIG. 3. Rather, it may have moulded features which mean that only a positive terminal can be received in one end region of one battery location, and only a negative terminal can be received in the corresponding end region of another battery location. Furthermore the two battery locations may be separated by a dividing wall. The intention is to make it impossible for incorrect battery insertions to be made.

FIGS. 10*a*, 10*b*, 11*a* and 11*b* show a further embodiment of the emanator and wick, together with a support and cap for the emanator. In this embodiment all of the remaining parts of the apparatus are the same, it is simply that the emanator 28 has been replaced with a different shape of emanator having more functionality. The wick 26 is also the same as previously shown. The emanator 28 works to emit fragrance in the same way as described above.

Figure 10A:
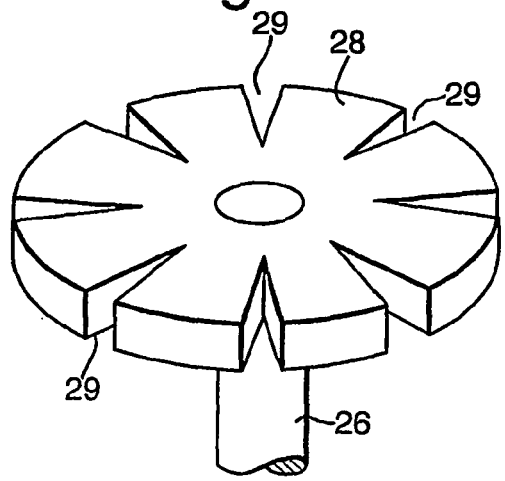
FIGS. 10a and 10b are schematic partial perspective cross-sectional views of a further embodiment of emanator in a second configuration.
Figure 10B:
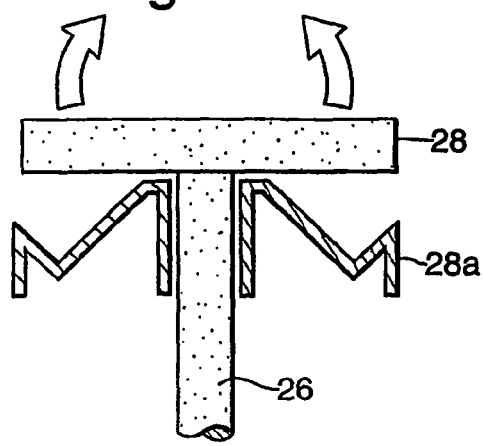
Figure 11A:
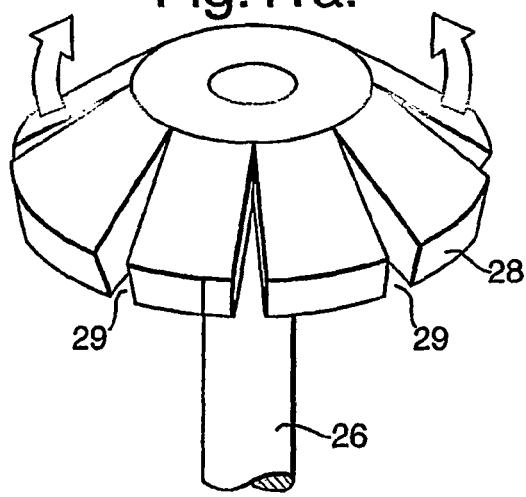
FIGS. 11a and 11b are views corresponding to those in FIGS. 10a and 10b of the further embodiment of emanator in a first configuration.
Figure 11B:
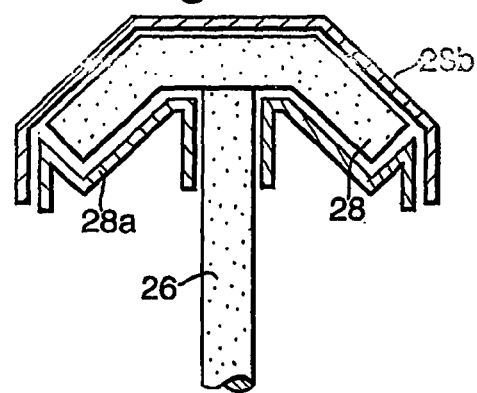

The differences in the emanator 28 shown in FIGS. 10*a* to 11*b* are that the emanator 28 is made of a flexible, resilient material, which may have "memory" that causes it to flex between the configuration shown in FIGS. 11*a* and 11*b*, which is a storage, or inoperative, configuration and the configuration shown in FIGS. 10*a* and 10*b*, which is an emanating, or operative, configuration.

A user would purchase the apparatus with the emanator 28 in the configuration shown in FIGS. 11*a* and 11*b* i.e. with the emanator 28 flexed downwards into an emanator seat 28*a*. The emanator seat 28*a* has a central opening through which the wick 26 protrudes. The emanator seat 28*a* may sit on top of the reservoir 24 (not shown in the figures for clarity). The emanator seat 28*a*, in conjunction with an emanator lid 28*b* holds the emanator 28 in the configuration shown in FIGS. 11*a* and 11*b*. The emanator lid 28*b* may engage the emanator seat 28*a* by means of interengaging threads.

In this embodiment as can be seen from FIGS. 10*a* and 11*a* the emanator 28 comprises a number of fingers or radial spokes extending away from a centre part of the emanator 28, with the fingers having cut-outs 29 therebetween. The presence of the fingers and their cut-outs allows the emanator 28 to be held in the dome shaped configuration shown in FIGS. 11*a* and 11*b* with the emanator lid 28*b* holding the emanator 28 in that position.

When a user desires to release the emanator 28 the emanator lid 28*b* is unscrewed from the emanator seat 28*a* and removed. Removal of the emanator lid 28*b* allows the emanator 28 to assume its preferred flat configuration as shown in FIG. 10*a* with the fingers extended in a flat configuration and the cut-outs 29 open. The cut-outs 29 are used to allow the dome shaped figuration in FIG. 11*a* and 11*b* to be achieved.

Given the resilience of the emanator 28 it has a tendency to assume the configuration shown in FIG. 10*a*. The presence of the cut-outs 29 has advantages in that a greater surface area is provided for the emanation of the evaporable chemical agent.

As can be seen in FIG. 10*b* beneath the emanator 28 when extended and above the emanator seat 28*a* there is an air space, which further enhances the circulation of air and thus emanation of the chemical agent.

This embodiment has advantages in that greater air circulation is provided by the presence of cut outs in the emanator 28. Also, the emanator 28 is held in the emanator seat 28*a* during transit and storage, which has significant advantages and prevents leakage of the chemical agent. The presence of the emanator seat 28*a* removes the potential presence of pockets in which the chemical agent could collect, the pockets being removed because they are filled with the emanator 28 when it is in the stored position shown in FIGS. 11*a* and 11*b*.

Figure 12A:
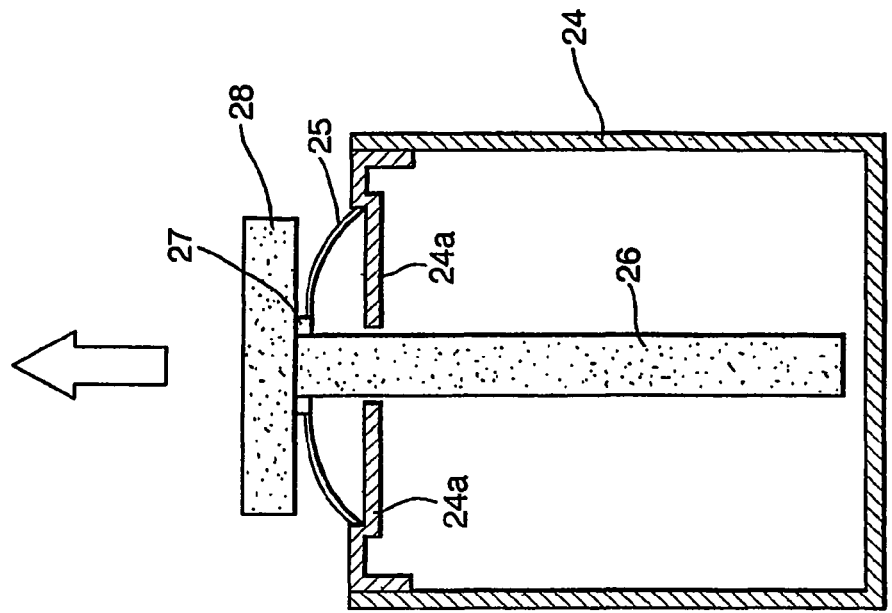
FIGS. 12a and 12b are cross-sectional side views of a still further embodiment showing a reservoir with a wick and emanator in lowered and raised configurations respectively.
Figure 12B:
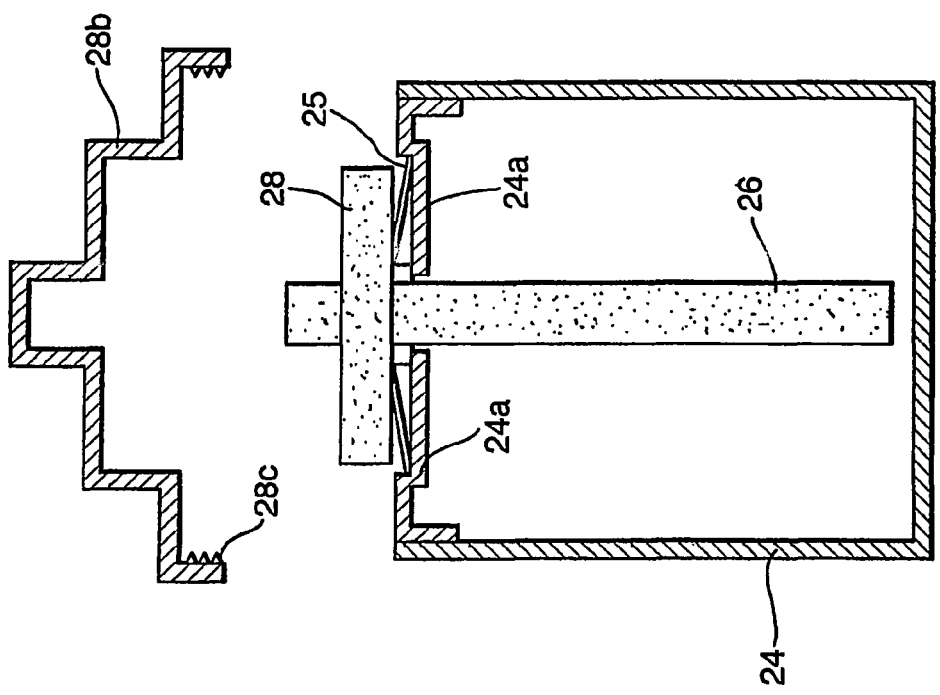
Figure 13:
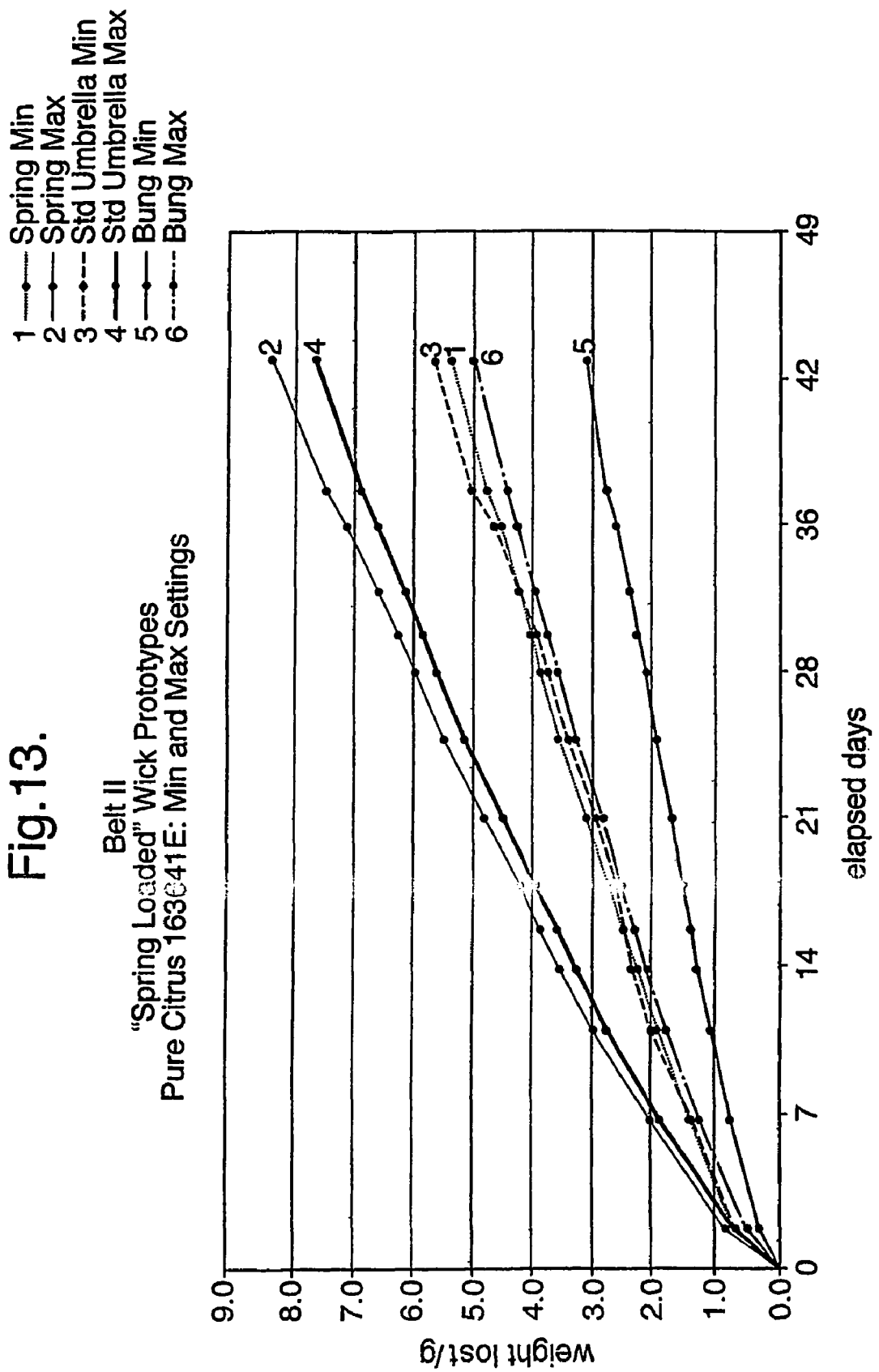
FIGS. 13 to 18 show graphs of output of the emanator of the first embodiment, the still further embodiment and another apparatus for different fragrances.
Figure 14:
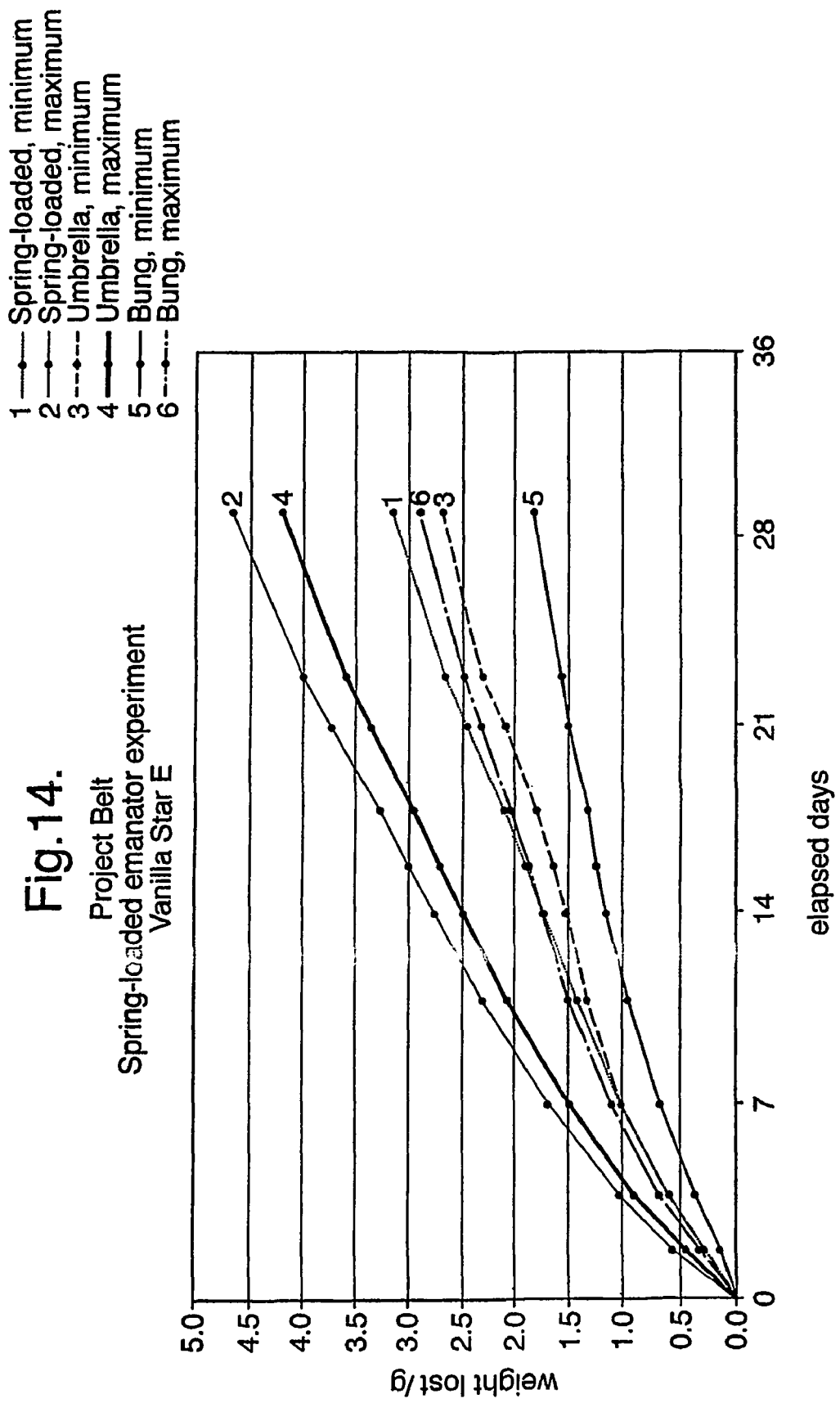
Figure 15:
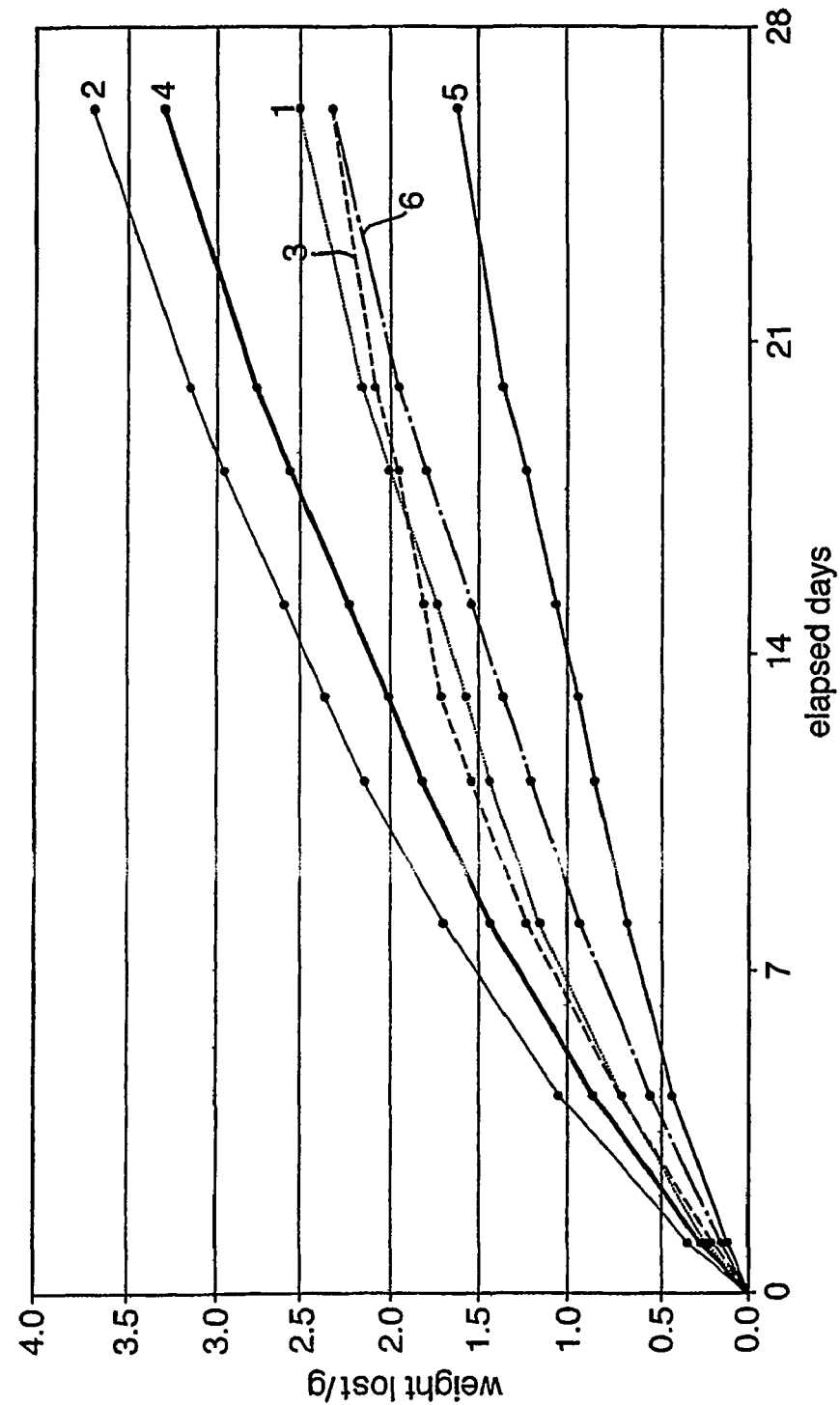
Figure 16:
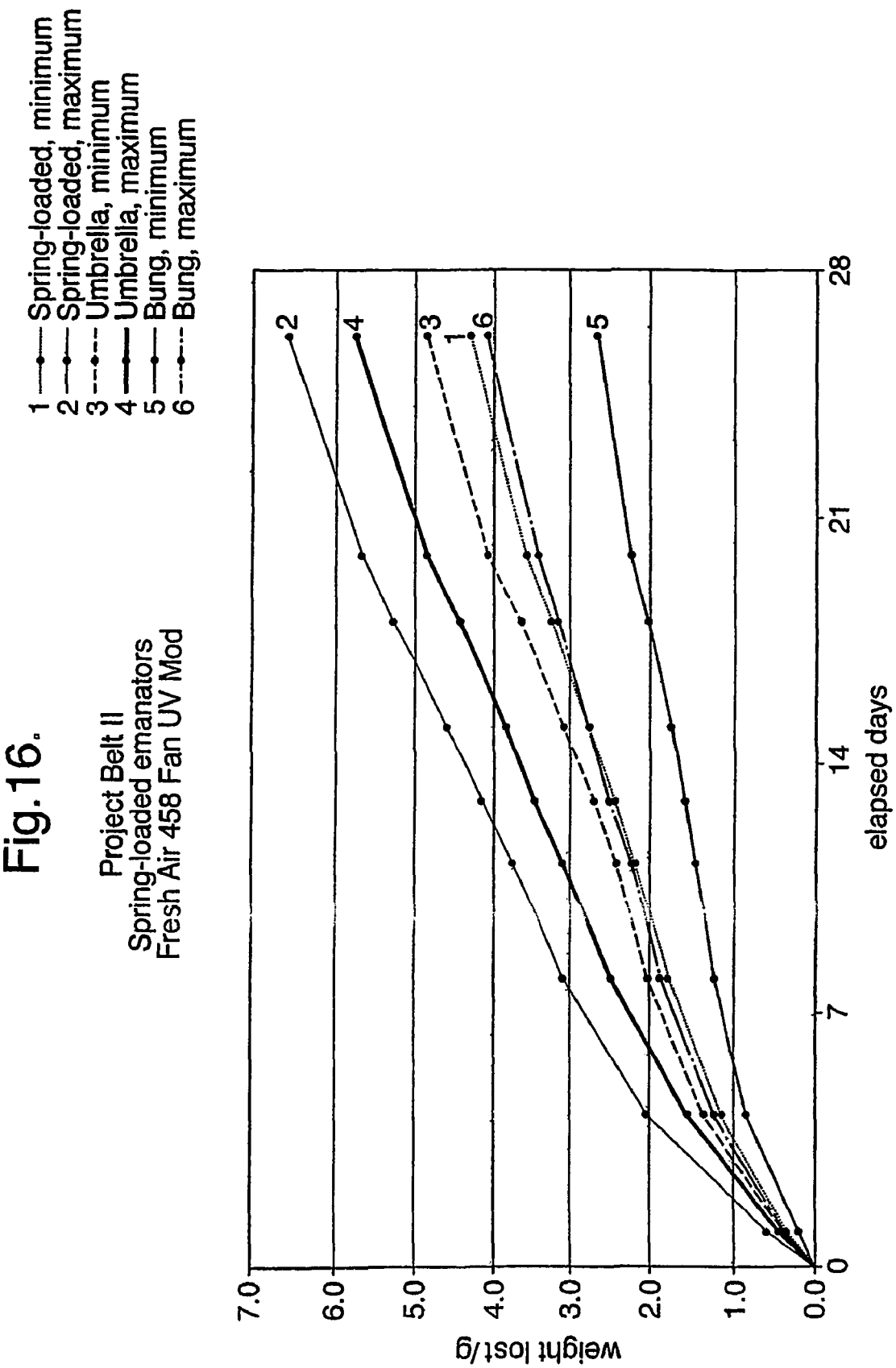
Figure 17:
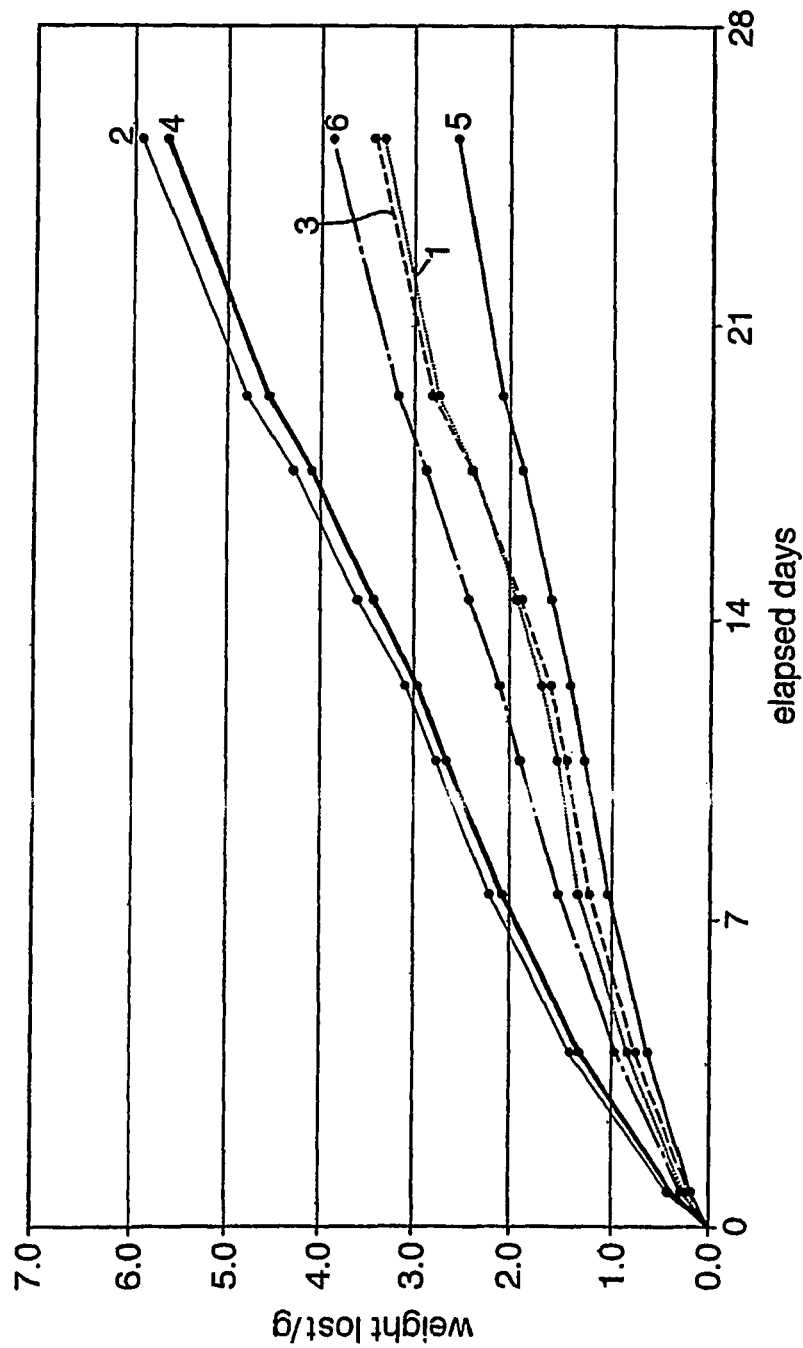
Figure 18:
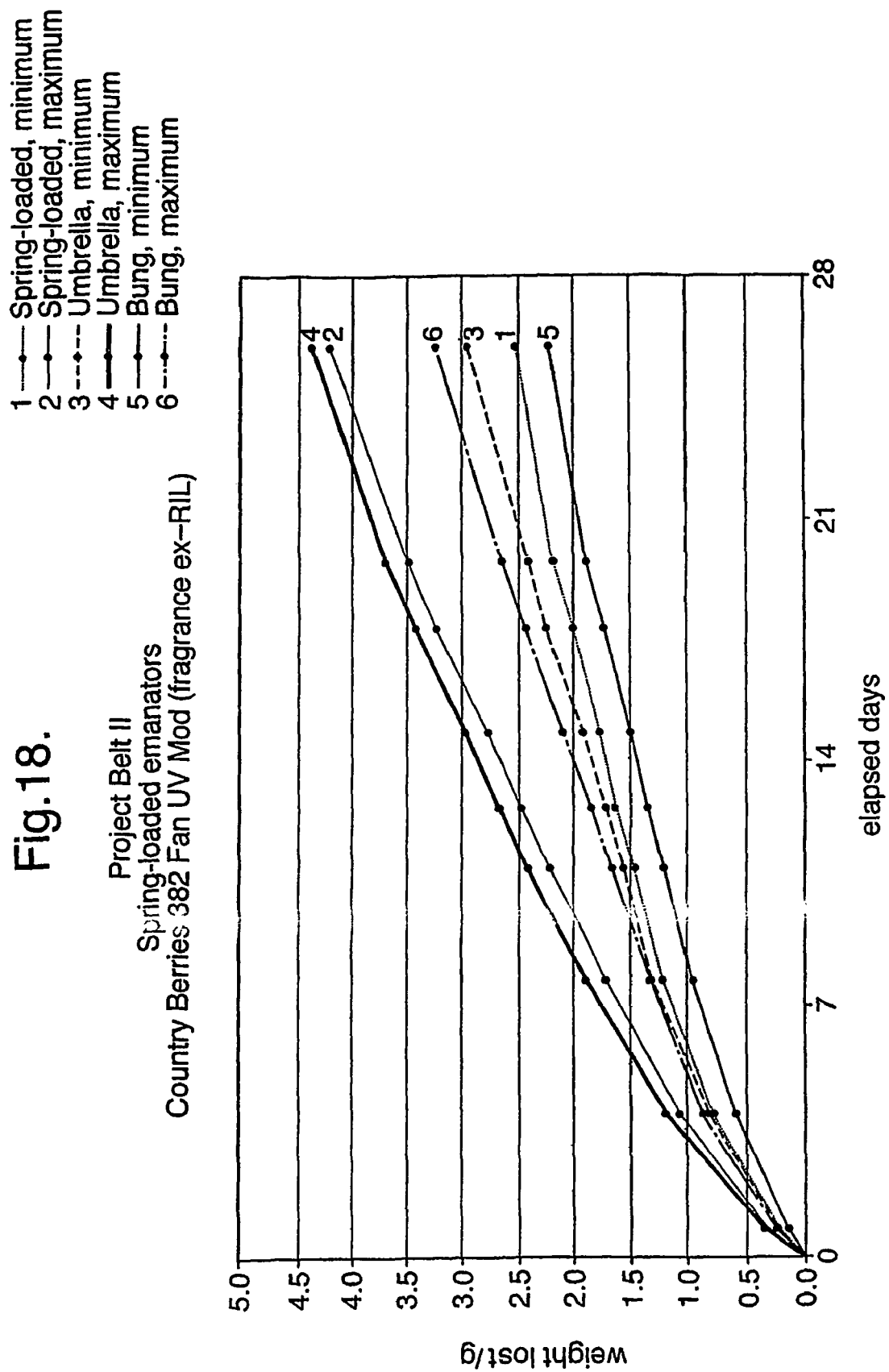

FIGS. 12*a* and 12*b* show a still further embodiment. In this embodiment the wick 26 and emanator 28 again have closed and open configurations shown respectively in FIGS. 12*a* and 12*b*. In these figures only the reservoir 24, wick 26 and emanator 28 (together with other parts to be described below) have been shown. The remainder of the parts of the apparatus are as described above in relation to previous embodiments. In FIG. 12*a* the reservoir 24 is shown containing the wick 26 which is spaced a chosen distance from the base of the reservoir to allow for manufacturing tolerances whilst at the same time allowing for the take up of a majority of the chemical agent to be stored therein. The wick 26 extends out of the reservoir 24 through an opening therein. The wick 26 also extends through the emanator 28 through a collar 27 surrounding a central opening in the emanator 28. An upper wall of the reservoir 24 incorporates a stepped recess 24*a* in which is received a resilient bias 25. An emanator lid 28*b* is shown above the remainder of the parts of FIG. 12*a* for clarity, but in reality the emanator lid 28*b* is secured to the reservoir 24 by means of interengaging threads shown at 28*c* on the emanator lid 28*b*.

The resilient bias 25 is held down by the emanator 28, which itself is held down against the upward force of the resilient bias 25 by the emanator lid 28*b*. The emanator 28 in this embodiment is permitted to move relative to the wick 26, which wick 26 is held in position relative to the reservoir 24, rather than held in position relative to the emanator 28. Thus, with the emanator lid 28*b* in the closed configuration with the threads 28*c* of the lid 28*b* engaged on the reservoir 24 the emanator 28 is held down. This has the advantage of eliminating open pockets in which the chemical agent may collect during transit or storage to be undesirably released when a user removes the lid 28*b* causing a spill.

On removal of the emanator lid 28*b* the resilient bias 25 pushes the emanator 28 upwards along the wick 26 to an end thereof. As can be seen in FIG. 12*b* the resilient bias 25 is extended and the emanator 28 includes the collar 27 to which is secured, or against which abuts, the resilient bias 25. The collar 27 also allows movement of the emanator 28 relative to the wick 26. Good air flow around the emanator 28 is permitted by the resilient bias 25, because it pushes the emanator 28 upwards to allow greater airflow around the emanator 28 than would have been achieved otherwise.

The resilient bias 25 is shown as a domed structure in FIG. 12*b*, although there is no limitation to the type of shape that can be used, for example a coiled spring could be used. A useful form of coiled spring that has been used is a conical spring which allows less space to be taken up by the compressed spring because its coils sit neatly within one another.

In this embodiment the emanator 28 is made of the same material as discussed in relation to the first embodiment i.e. of the sintered material. The embodiment described in relation to FIGS. 12*a* and 12*b* has an advantage in that the wick 26 is not deformable, allowing the use of existing emanator materials.

FIGS. 13 to 18 show graphs of weight loss for three different types of devices which are operated using the fan 20 on its minimum and maximum settings. The graphs show operation over a period of 43 days with weight loss being shown in grammes. The reference on the graphs to "spring min" and "spring max" refers to performance figures for the device shown in FIGS. 12a and 12b. The reference to "standard umbrella min" and "standard umbrella max" in the graphs refers to performance figures for the device having an emanator arranged in a fixed position as shown in FIG. 2. The reference to "bung min" and "bung max" in the graphs refers to performance figures for an emanator which is located having its lower face abutting a top part of the reservoir 24, so there is no air flow over the lower face of the emanator.

In the device for which results are shown by lines 5 and 6 (bung min/bung max) there is less surface area of the emanator 28, because the lower surface abuts the reservoir. Thus, the results in FIGS. 13 to 18 for this version show consistently less weight loss over the trial period.

The embodiment shown in FIGS. 12a and 12b has greater weight loss, which is seen as advantageous, than the fixed emanator 28 shown in FIG. 2. The reason for this is believed to be that there is greater air circulation space in the embodiment shown in FIGS. 12a and 12b compared to that shown in FIG. 2. Thus, it is seen as advantageous to have the moveable spring loaded emanator 28 that is shown in FIGS. 12 and 12b.

The graphs in FIGS. 13 to 18 relate to results for the devices indicated when used with the following fragrance, in the order of the figures: Pure Citrus, Vanilla, Sweet Spring, Fresh Air, Fresh Melon, Country Berries, said fragrances being produced by the present applicant.

The unit comprising reservoir 24, wick 26, resilient bias 25, emanator 28 and the lid 28b may be sold as a replacement section for the apparatus described in relation to FIGS. 1 to 7. Alternatively the unit may be used as an emanator device that does not include a fan.

The invention claimed is:

1. Apparatus for emitting a chemical agent as a vapour, the apparatus comprising:
   a cartridge comprising a reservoir containing the chemical agent in liquid form and a battery compartment;
   a wick in communication with the chemical agent;
   an emanator carried by the wick and located outside the reservoir;
   an electrically operable fan to impel air over the emanator; and,
   a base, wherein the base is formed with a socket to receive a bottom region of the cartridge.

2. Apparatus according to claim 1, wherein the emanator is larger in cross-section than the wick.

3. Apparatus according to claim 2, wherein the area of the emanator, in plan view, is at least two times the cross-sectional area of the wick.

4. Apparatus according to claim 1 wherein the emanator has a generally flat upper surface over which air flows.

5. Apparatus according to claim 4, wherein the emanator has a plurality of surfaces over which air flows transversely.

6. Apparatus according to claim 1 wherein the emanator has two generally planar surfaces, transverse to the axis of the wick.

7. Apparatus according to claim 1 wherein the emanator is a capillary body without non-capillary through-bores.

8. Apparatus according to claim 1 wherein the apparatus includes a base on which are mounted the fan, and a motor therefor.

9. Apparatus according to claim 1 wherein the reservoir is formed with an overhanging wall portion generally facing the fan.

10. Apparatus according to claim 1 which comprises a removable cover.

11. Apparatus according to claim 10, wherein the cover has a plurality of air inlet channels.

12. Apparatus according to claim 11, wherein the cover has main side walls having said air inlet channels, and a front wall which has an outlet opening.

13. Apparatus according to claim 11 wherein the air inlet channels are such as to deliver air into the apparatus in one or more directions generally transverse to the direction(s) in which air leaves the apparatus.

14. Apparatus according to claim 11, wherein the air inlet channels are such that air drawn through them follows a non-straight and/or sinuous pathway.

15. Apparatus according to claim 1 further comprising means for adjusting the volatile output of the apparatus.

16. Apparatus according to claim 15, wherein the means for adjusting the volatile output of the apparatus comprises means for controlling the periods for which the fan operates.

17. Apparatus for emitting a chemical agent as a vapour, the apparatus comprising:
   reservoir containing the chemical agent in a liquid form;
   a wick in communication with the chemical agent;
   an emanator carried by the wick and located outside the reservoir; and
   an electrically operable fan to impel air over the emanator;
   wherein the emanator is operable to move between a first, inoperative, configuration and a second operative, configuration by a resilient bias.

18. Apparatus according to claim 17 wherein the emanator is operable to move relative to the wick.

19. Apparatus according to claim 18, in which the emanator is held in the first configuration by a cover.

20. A method of delivering a vapour into an air space, the method comprising the steps of:
   providing an apparatus according to claim 1; and,
   operating the apparatus to delivery a chemical agent as a vapour from the apparatus.

21. A cartridge adapted to be coupled to a base unit to form an apparatus according to claim 1 wherein the apparatus comprises a reservoir, a chemical agent within the reservoir, a wick partly in communication with the chemical agent, an emanator carried by the wick and a battery compartment containing battery means.

22. Apparatus for emitting a chemical agent as a vapour, the apparatus comprising:
   a removable refill cartridge comprising:
      a reservoir containing the chemical agent in liquid form;
      a wick in communication with the chemical agent;
      an emanator carried by the wick and located outside the reservoir;
      battery means; and,
   a base comprising:
      an electrically operable fan to impel air over the emanator; and,
      a removeable cover being open at its base to allow the cover to pass over the refill cartridge and the base.

* * * * *